US00PP33294P2

(12) United States Plant Patent
Van Swieten

(10) Patent No.: US PP33,294 P2
(45) Date of Patent: Jul. 27, 2021

(54) ***PHALAENOPSIS* ORCHID PLANT NAMED 'PHALIPZYL'**

(50) Latin Name: *Phalaenopsis hybrid*
Varietal Denomination: PHALIPZYL

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/974,256

(22) Filed: Dec. 2, 2020

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named 'PHALIPZYL', QZ PBR 2019/2299, filed Sep. 19, 2019.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALIPZYL', particularly characterized by small, dark red flowers with few light reddish-purple flecks at the center and dark purple-red lips, a convex flower shape in lateral view, whiskers with dotted tips, and is propagated by meristem tissue culture, is disclosed.

3 Drawing Sheets

Genus and species: *Phalaenopsis* hybrid.
Variety denomination: 'PHALIPZYL'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALIPZYL'.

The new *Phalaenopsis* plant is a product of a planned breeding program conducted by the inventor in Bleiswijk, the Netherlands. The objective of this breeding program was to create a new *Phalaenopsis* plant with many attractive, small, dark red flowers with few light reddish-purple flecks at the center and dark purple-red lips, suitable for potted plant production.

The new *Phalaenopsis* plant 'PHALIPZYL' is a result of cross-pollination made by the inventor in October 2012 in Bleiswijk, the Netherlands, of the proprietary female, or seed parent, *Phalaenopsis* hybrid '01-4404' (unpatented) with the proprietary male, or pollen parent, *Phalaenopsis* hybrid 'PHALDUKAI' (U.S. Plant Pat. No. 28,157).

The new *Phalaenopsis* was selected by the inventor as a single plant within the progeny of the stated cross-pollination in a controlled greenhouse in Bleiswijk, the Netherlands, in July 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 19, 2019 (Application no. 2019/2299), by Applicant who obtained the subject matter disclosed directly from the inventor. 'PHALIPZYL' has not been made publicly available or sold anywhere in the world prior to the effective filing date of this application with the exception of sales or disclosures made one year or less before the effective filing date of this claimed invention by Applicant who obtained 'PHALIPZYL' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALIPZYL' as a new and distinct variety of *Phalaenopsis* plant:

1) Small, dark red flowers with few light reddish-purple flecks at the center and dark purple-red lips;
2) Flower shape in lateral view is convex; and
3) Whiskers tips are dotted.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 45-week-old plants in November 2020. Colors in the photographs may differ from the color values cited in the detailed botanical description, which accurately describe the actual colors of the new variety.

DESCRIPTION OF THE NEW VARIETY

Figure 1:
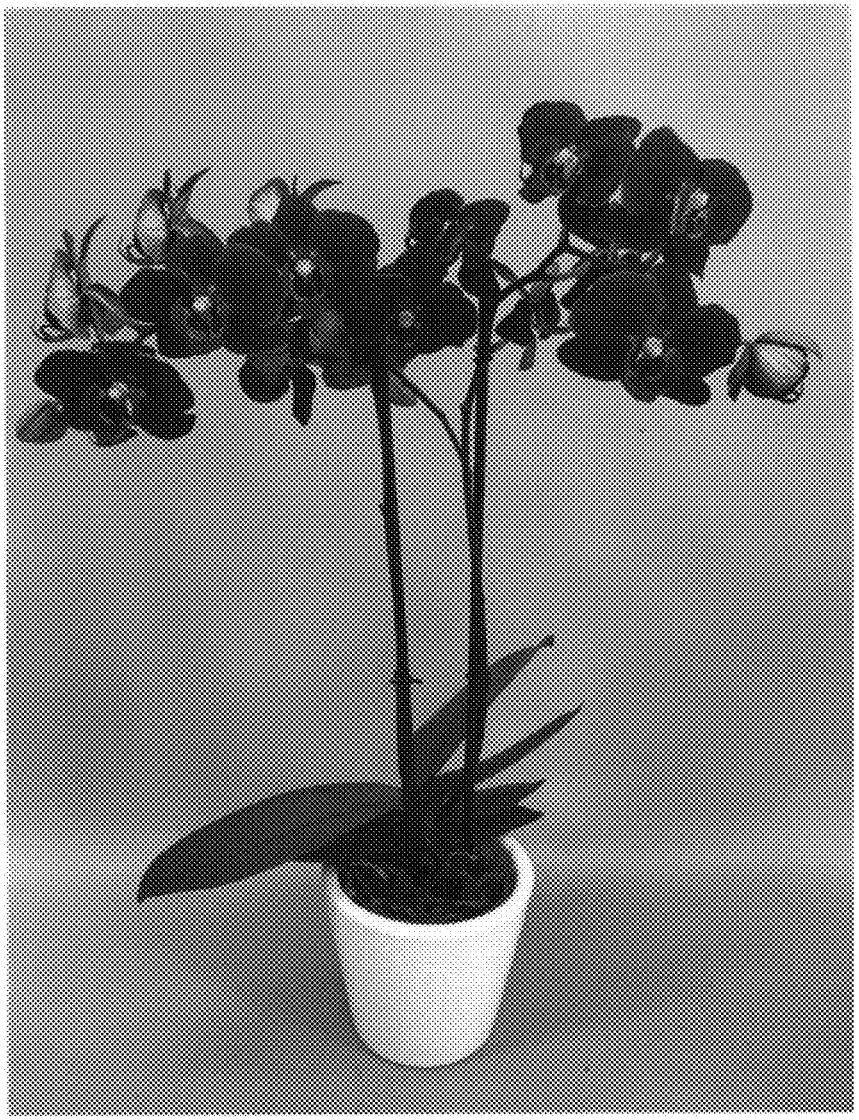
FIG. 1 shows the overall plant habit, including blooms, buds, and foliage of 'PHALIPZYL'.
Figure 2:
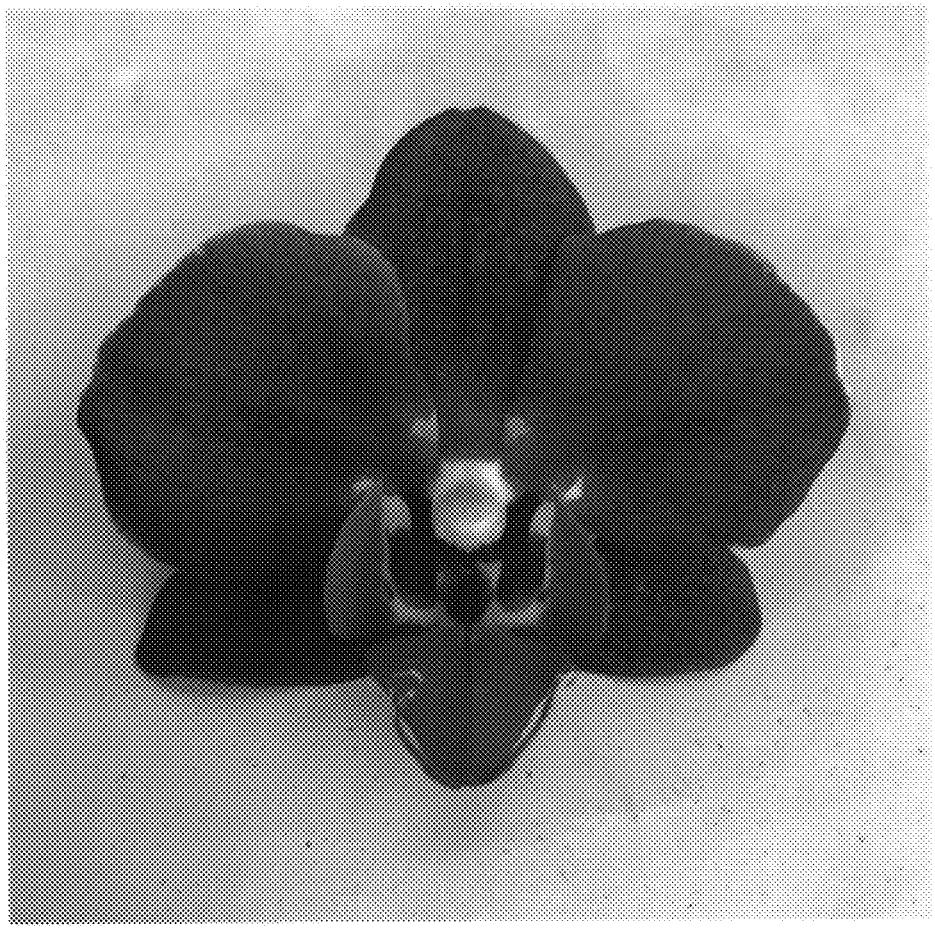
FIG. 2 shows a close-up of a flower of 'PHALIPZYL'.
Figure 3:
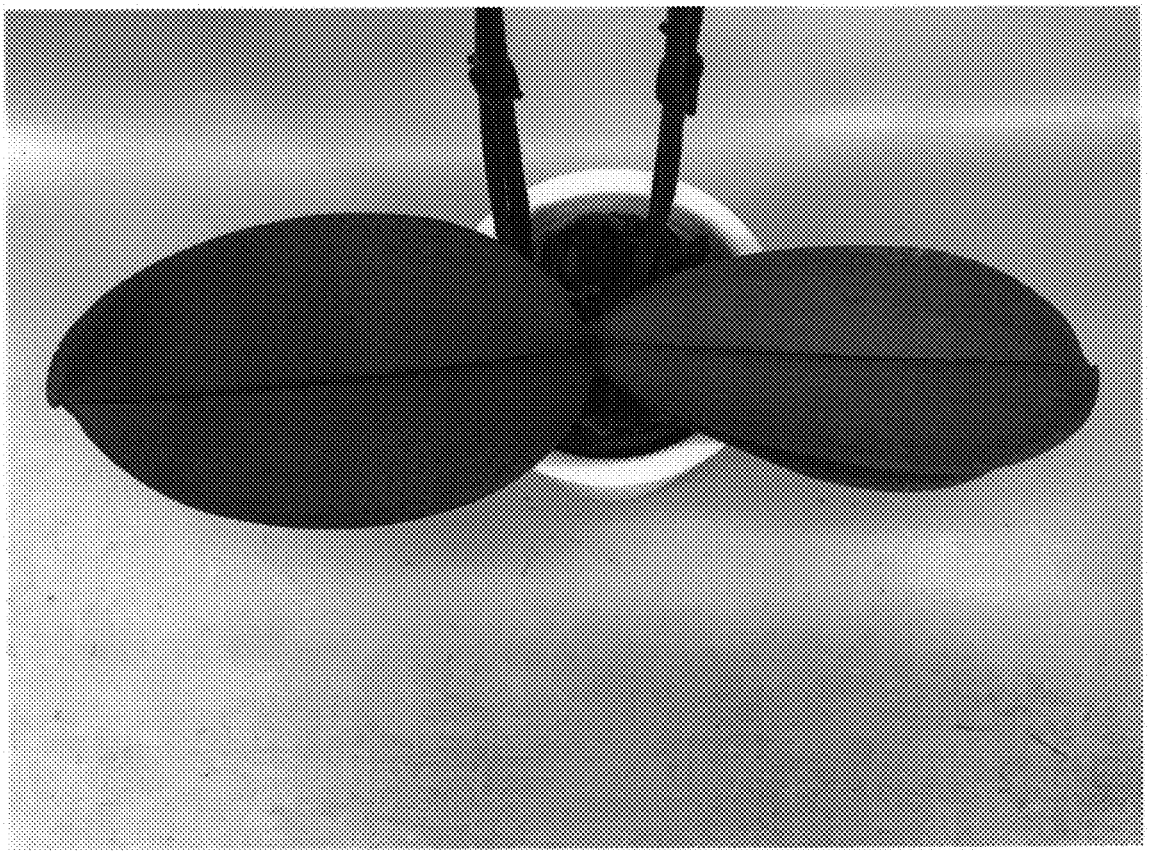
FIG. 3 shows an overhead view of the leaves of 'PHALIPZYL'.

The following detailed description sets forth the distinctive characteristics of 'PHALIPZYL'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in November 2020 on flowering plants which were planted in 9-centimeter (diameter) pots. After in vitro propagation, the plants were grown in nursery trays for 18-20 weeks, followed by transplantation to 9-centimeter pots and grown in a greenhouse between 27° C. to 29° C. for 25 weeks, continued by a cooling period of 6 weeks between 18° C. to 20° C. and 11 weeks in a greenhouse of 21° C. Flowering occurs after 42 weeks in 9-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALIPZYL'.

Parentage:

*Female parent*.—*Phalaenopsis* cultivar '01-4404' (unpatented).

*Male parent*.—*Phalaenopsis* cultivar 'PHALDUKAI' (U.S. Plant Pat. No. 28,157).

Propagation:

*Type*.—Meristem tissue culture.

Roots:

*Root description*.—Greyed-green (something between RHS 190B and 190C) colored roots with branching lateral roots having yellow-green (RHS 145A) with a hint of purplish-red (RHS N77B) colored root tips.

Plant:

*Commercial crop time to flowering*.—Following asexual propagation (in vitro), the rooted cuttings grow for 18-20 weeks. After transplantation into 9-cm pots, the plants are finished after 40 to 42 weeks.

*Growth habit of the peduncle*.—Upright to slightly pendent with raceme and panicle inflorescence.

*Height (from soil level to top of inflorescence)*.—Approximately 40.0 cm to 45.0 cm.

*Width (measured from leaf tips)*.—About 29.0 cm to 31.0 cm.

*Vigor*.—Strong.

Leaves:

*Mature leaves*.—Quantity per plant: 8 to 10 leaves are produced before flowering. Length (fully expanded): 14.0 cm to 16.0 cm. Width: 7.0 cm to 8.0 cm. Position of the broadest part of the leaf: Toward apex. Shape: Obovate. Base shape: Moderately elongated. Apex: Obtuse unequal. Leaf blade angle with the petiole (measured from the horizontal position): Between 20 degrees and 35 degrees. Leaf margin: Entire. Color: Upper surface: RHS 147A with a touch of reddish-brown (RHS 200A) at margin toward the tip. Lower surface: RHS 147B and purple-brown (something in between RHS N77A and 200A). Texture: Upper surface: A little bit rough. Lower surface: Smooth. Thickness: 1.9 mm to 2.4 mm. Variegation: Absent. Venation: Pattern: Parallel. Color of the midvein: Upper surface: Reddish-brown (RHS 200A). Lower surface: Purple-brown (something in between RHS 200A and N77A).

Peduncle:

*Quantity per plant*.—1 to 2.

*Number of flowers per peduncle*.—9 to 13.

*Length*.—40.0 cm to 45.0 cm.

*Diameter*.—4.0 mm to 5.0 mm.

*Strength*.—Strong.

*Aspect*.—Upright to slightly pendent.

*Texture*.—Smooth.

*Color*.—Mix of brown (RHS 200A) and green (RHS 146C).

*Internode length*.—2.0 cm to 3.0 cm.

Inflorescence description:

*Appearance*.—Upright to slightly pendent, raceme and panicle inflorescence with bilaterally symmetrical flowers that open in succession beginning with the lowermost flower.

*Number of inflorescences*.—1 to 2.

*Inflorescence size*.—Height (from base to tip): 190.0 mm to 230.0 mm.

*Flowering time*.—First flowers can be expected 7 to 8 months after planting in a 9-cm pot.

*Flower*.—Height: 48.0 mm to 53.0 mm. Diameter: 58.0 mm to 63.0 mm. Depth of lip: 17.0 mm to 19.0 mm.

*Flower longevity*.—On the plant: 11 to 13 weeks.

*Flower shape in lateral view*.—Convex.

*Fragrance*.—Absent.

*Flower bud*.—Average size: Medium. Length: 19.0 mm to 21.0 mm. Width: 15.0 mm to 17.0 mm. Shape: Egg shaped. Color: Yellow-green (RHS 146D) and purple (RHS N77A) with dark red shade (RHS 183B) and dark red stripes (RHS 187B).

*Petals*.—Arrangement: Open/free. Shape: Semi-circular. Apex: Rounded to emarginated asymmetric. Margin: Moderately to strongly undulated. Length (from base to tip): 26.0 mm to 28.0 mm. Width: 32.0 mm to 34.0 mm. Position of the broadest part of the petal: Toward the base. Color (when fully opened): Upper surface: Basic color: Dark red (something in between RHS 187B and 187C). Over color: Few light reddish-purple flecks (RHS N78D) at the base. Lower surface: Basic color: Very light purple (RHS 76D) at the base. Over color: Very light purple (RHS 76B) and diluting reddish-purple (RHS N79D) toward the margin. Number of spots, flecks, and stripes on the petals (upper surface): Few flecks at the base. Color of spots, flecks, and stripes on the petals (upper surface): RHS N78D. Density of netting of the petals (upper surface): None. Color of the netting (upper surface): Not applicable.

*Dorsal sepal*.—Shape: Elliptic. Apex: Emarginated symmetric. Margin: Moderately undulated. Length (from base to tip): 30.0 mm to 32.0 mm. Width: 22.0 mm to 24.0 mm. Position of the broadest part of the dorsal sepals: At the middle. Color (when fully opened): Upper surface: Basic color: Dark red (something in between RHS 187A and 187B). Over color: Absent. Lower surface: Basic color: Reddish-purple (something in between RHS N78C and N79D). Over color: Light yellow-green (something in between RHS 145C and 145D). Number of spots and stripes on the dorsal sepals (upper surface): None. Color of spots and stripes on the dorsal sepals (upper surface): Not applicable. Density of netting of the dorsal sepals (upper surface): None. Color of the netting: Not applicable.

*Lateral sepals*.—Shape: Ovate. Apex: Obtuse asymmetric. Margin: Weakly undulated. Length (from base to tip): 31.0 mm to 33.0 mm. Width: 19.0 mm to 21.0 mm. Position of the broadest part of the lateral sepals: Toward the base. Color (when fully opened): Upper surface: Basic color: Dark red (something in between RHS 187A and 187B). Over color: Absent. Lower surface: Basic color: Reddish-purple (RHS N79D). Over color: Light yellow-green (something in between RHS 145C and 145D); dark red-purple midvein (RHS 187C) toward the tip. Number of spots and stripes on the lateral sepals (upper surface): None. Color of spots and stripes on the lateral sepals (upper surface): Not applicable. Density of netting of the lateral sepals (upper surface): None. Color of the netting (upper surface): Not applicable.

*Labellum* (*lip*).—Whiskers: Present. Length of whiskers: 13.0 mm to 15.0 mm. Color of whiskers: Dark red (RHS 187B) with light greenish-yellow (RHS 8B) dotted tips (RHS 187B). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated (widely wavy). Length: 17.0 mm to 19.0 mm. Width: 11.0 mm to 13.0 mm. Color: Upper surface: Touch of light greenish-yellow (RHS 4D) and white (RHS NN155C) with dark red fleck (RHS 187A) at the base; dark red (RHS 59A) and dark purplish-red (RHS N79C) toward the margin. Lower surface: White (RHS NN155C) with a hint of light greenish-yellow (RHS 4D) at the base toward margin on one side; dark red (RHS 59A) on the other side and dark purplish-red (RHS N79C) toward the tip. Number of spots, flecks, and stripes on the lateral lobe: One fleck. Color of spots, flecks, and stripes on the lateral lobe: RHS 187A. Density of netting of the lateral lobe: None. Color of the netting: Not applicable.

*Apical lobe*.—Shape: Triangular. Margin: Entire. Length: 17.0 mm to 19.0 mm. Width: 16.0 mm to 18.0 mm. Color: Upper surface: Red (RHS 59A) at the base; dark purplish-red (RHS N79C) toward whiskers. Lower surface: Red (RHS 59A) at the base; purplish-red (RHS N78A) toward whiskers. Number of spots and stripes on the apical lobe: None. Color of spots and stripes on the apical lobe: Not applicable. Density of netting of the apical lobe: None. Color of the netting: None.

*Callus*.—Average size: Medium. Height: 6.0 mm to 7.0 mm. Length: 5.0 mm to 6.0 mm. Width: 3.0 mm to 4.0 mm. Color: Light greenish-yellow (something in between RES 4C and 4D) on sides toward tips and dark red (RHS 187B) at the middle.

Reproductive organs:

*Column*.—Length: 8.0 mm to 10 0 mm. Diameter: 5.0 mm to 6.0 mm. Color: White (RHS NN155C) at the base and reddish-purple region (RHS N78B) toward the tip.

*Pollinia*.—Quantity: 2. Diameter: 0.7 mm to 0.9 mm. Color: Orange-yellow (RHS 23A).

*Ovary*.—Length: 10.0 mm to 12.0 mm. Diameter: 2.0 mm to 2.3 mm.

*Pedicel*.—Length: 31.0 mm to 33.0 mm. Diameter: 2.4 mm to 2.7 mm. Texture: Smooth. Color: Light yellow-green (something in between RHS 145C and 145D) with a touch of dark purplish-red (something in between RHS N78B and N79C) toward the base and light reddish-purple (RHS N78D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALIPZYL' differs from the female parent plant '01-4404' (unpatented), in that 'PHALIPZYL' has a convex flower shape in lateral view, whereas '01-4404' has flat flower shape in lateral view. Additionally, 'PHALIPZYL' has larger flowers than '01-4404'.

'PHALIPZYL' differs from the male parent plant 'PHALDUKAI' (U.S. Plant Pat. No. 28,157) in that 'PHALIPZYL' has a convex flower shape in lateral view, whereas 'PHALDUKAI' has a concave flower shape in lateral view. Additionally, 'PHALIPZYL' has smaller flowers than 'PHALDUKAI'.

'PHALIPZYL' is most similar to the commercial *Phalaenopsis* plants named 'PHALFENCK' (U.S. Plant Pat. No. 27,460) and 'PHALFIQALO' (unpatented). 'PHALIPZYL' differs from the commercial variety 'PHALFENCK' in that 'PHALIPZYL' has weakly spatulate lateral lobes, whereas 'PHALFENCK' has spatulate lateral lobes. Additionally, 'PHALIPZYL' has smaller flowers and shorter leaves than 'PHALFENCK'.

'PHALIPZYL' differs from the commercial variety 'PHALFIQALO' in that 'PHALIPZYL' has triangular apical lobes, whereas 'PHALFIQALO' has ovate apical lobes. Additionally, 'PHALIPZYL' has larger flowers, longer whiskers, and longer leaves than 'PHALFIQALO'.

I claim:

1. A new and distinct variety of *Phalaenopsis* plant named 'PHALIPZYL', substantially as described and illustrated herein.

* * * * *